US011819318B2

(12) United States Patent
Konecky

(10) Patent No.: US 11,819,318 B2
(45) Date of Patent: Nov. 21, 2023

(54) OPTICAL IMAGING FROM LIGHT COHERENCE

(71) Applicant: Open Water Internet Inc., San Francisco, CA (US)

(72) Inventor: Soren Konecky, Alameda, CA (US)

(73) Assignee: Open Water Internet Inc., San Francisco, CA (US)

( * ) Notice: Subject to any disclaimer, the term of this patent is extended or adjusted under 35 U.S.C. 154(b) by 250 days.

(21) Appl. No.: 16/904,572

(22) Filed: Jun. 18, 2020

(65) Prior Publication Data

US 2021/0330202 A1   Oct. 28, 2021

Related U.S. Application Data

(60) Provisional application No. 63/016,011, filed on Apr. 27, 2020.

(51) Int. Cl.
    *A61B 5/026*        (2006.01)
(52) U.S. Cl.
    CPC .................................. *A61B 5/0261* (2013.01)
(58) Field of Classification Search
    CPC ........................... A61B 5/0066; B05C 5/0216
    USPC ......................................................... 600/478
    See application file for complete search history.

(56) References Cited

U.S. PATENT DOCUMENTS

| | | |
|---|---|---|
| 3,573,362 A | 4/1971 | Burchardt |
| 6,172,760 B1 | 1/2001 | Son |
| 6,608,774 B1 | 8/2003 | Rentzepis |
| 6,956,650 B2 | 10/2005 | Boas |
| 7,119,906 B2 | 10/2006 | Pepper |
| 7,460,248 B2 | 12/2008 | Kurtz |
| 7,551,809 B2 | 6/2009 | Taira |
| 7,610,082 B2 | 10/2009 | Chance |
| 7,647,091 B2 | 1/2010 | Ntziachristos |
| 7,728,986 B2 | 6/2010 | Asker |
| 7,804,070 B1 | 9/2010 | Pan |
| 7,821,640 B2 | 10/2010 | Koenig |
| 7,822,468 B2 | 10/2010 | Stammes |
| 7,826,878 B2 | 11/2010 | Alfano |
| 7,898,649 B2 | 3/2011 | Masumura |
| 7,965,389 B2 | 6/2011 | Da Silva |
| 7,983,740 B2 | 7/2011 | Culver |

(Continued)

OTHER PUBLICATIONS

Arridge et al. Nonuniqueness in diffusion-based optical tomography, Optics Letters, Jun. 1, 1998, vol. 23, No. 11, pp. 882-884.

(Continued)

*Primary Examiner* — Fabricio R Murillo Garcia
(74) *Attorney, Agent, or Firm* — FREESTONE INTELLECTUAL PROPERTY LAW PLLC

(57) ABSTRACT

Coherent light (e.g., laser light) is emitted into a tissue sample through an optical fiber. The tissue sample diffuses the coherent light. Different blood flow quantities generate different coherent light interference patterns. An image of a coherent light interference pattern is captured with an image sensor coupled to an optical fiber. The speckle contrast of the image quantifies coherent light interference pattern. The speckle contrast is determined and is mapped to blood flow quantities using one or more data models. A quantity of blood flow is identified in a tissue sample at least partially based on the speckle contrast value of the captured image.

16 Claims, 13 Drawing Sheets

(56) References Cited

U.S. PATENT DOCUMENTS

| | | |
|---|---|---|
| 7,928,896 B2 | 8/2011 | Jin |
| 8,014,847 B2 | 9/2011 | Shastri |
| 8,120,784 B2 | 2/2012 | Da Silva |
| 8,170,651 B2 | 5/2012 | Lorenzo |
| 8,239,006 B2 | 8/2012 | Zhu |
| 8,263,947 B2 | 9/2012 | Da Silva |
| 8,289,502 B2 | 10/2012 | Yoshida |
| 8,326,567 B2 | 12/2012 | Masumura |
| 8,330,642 B2 | 12/2012 | Jin |
| 8,355,131 B2 | 1/2013 | Bakker et al. |
| 8,357,915 B2 | 1/2013 | Guyon et al. |
| 8,374,409 B2 | 2/2013 | Jochemsen |
| 8,416,421 B2 | 4/2013 | Wang |
| 8,450,674 B2 | 5/2013 | Yang |
| 8,451,450 B2 | 5/2013 | Heng |
| 8,520,921 B2 | 8/2013 | Ziegler |
| 8,525,998 B2 | 9/2013 | Yaqoob |
| 8,527,242 B2 | 9/2013 | Granot |
| 8,531,662 B2 | 9/2013 | Van Der Mark |
| 8,563,932 B2 | 10/2013 | Fang |
| 8,634,077 B2 | 1/2014 | Hu |
| 8,649,015 B2 | 2/2014 | Ichihara |
| 8,917,442 B2 | 3/2014 | Baym |
| 8,717,574 B2 | 5/2014 | Yang |
| 8,814,795 B2 | 8/2014 | Derode |
| 8,817,255 B2 | 8/2014 | Masumura |
| 8,830,573 B2 | 9/2014 | Cui |
| 8,847,175 B2 | 9/2014 | Aidevant |
| 8,937,284 B2 | 1/2015 | Fang |
| 8,954,130 B2 | 2/2015 | Masumura |
| 8,976,433 B2 | 3/2015 | Masumura |
| 9,012,869 B2 | 4/2015 | Andersson-Engels |
| 9,036,970 B2 | 5/2015 | Guyon |
| 9,037,216 B2 | 5/2015 | Hielscher |
| 9,057,695 B2 | 6/2015 | Masumura |
| 9,131,851 B2 | 9/2015 | Fukutani |
| 9,134,229 B2 | 9/2015 | Lesage |
| 9,179,842 B2 | 11/2015 | Nakaji |
| 9,207,171 B2 | 12/2015 | Nadakuditi |
| 9,234,841 B2 | 1/2016 | Wang |
| 9,282,932 B2 | 3/2016 | Kudo |
| 9,297,752 B2 | 3/2016 | Shimokawa |
| 9,304,490 B2 | 4/2016 | Masumura |
| 9,313,423 B2 | 4/2016 | Wang |
| 9,335,604 B2 | 5/2016 | Popovich |
| 9,335,605 B2 | 5/2016 | Wang |
| 9,341,569 B2 | 5/2016 | Hooft |
| 9,354,166 B2 | 5/2016 | Judkewitz |
| 9,373,020 B2 | 6/2016 | Kudo |
| 9,407,796 B2 | 8/2016 | Dinten |
| 9,427,213 B2 | 8/2016 | Suzuki |
| 9,480,425 B2 | 11/2016 | Culver |
| 9,486,142 B2 | 11/2016 | Hielscher |
| 9,488,574 B2 | 11/2016 | Koehler |
| 9,509,956 B2 | 11/2016 | Piestun |
| 9,622,663 B2 | 4/2017 | Fang |
| 9,689,797 B2 | 6/2017 | Sun |
| 9,724,489 B2 | 8/2017 | Barbour |
| 9,730,649 B1 | 8/2017 | Jepsen |
| 9,750,413 B2 | 9/2017 | Sandusky |
| 10,420,469 B2 | 9/2019 | Sobek et al. |
| 10,477,173 B1* | 11/2019 | Ortiz Egea .......... H04N 5/2256 |
| 2004/0048842 A1* | 3/2004 | McMillan .......... A61K 41/0061 |
| | | 514/561 |
| 2004/0076390 A1* | 4/2004 | Dong Yang ........ G01N 21/4795 |
| | | 385/116 |
| 2010/0016732 A1 | 1/2010 | Wells |
| 2012/0052947 A1 | 3/2012 | Yun |
| 2012/0070817 A1 | 3/2012 | Wang et al. |
| 2014/0009808 A1 | 1/2014 | Wang et al. |
| 2014/0081096 A1 | 3/2014 | Baym |
| 2014/0114181 A1 | 4/2014 | Wu |
| 2014/0168660 A1* | 6/2014 | Yan ..................... G01B 9/02064 |
| | | 356/511 |
| 2014/0206890 A1 | 7/2014 | Augustin et al. |
| 2014/0206980 A1* | 7/2014 | Lee ...................... A61B 5/0261 |
| | | 600/407 |
| 2014/0303473 A1 | 10/2014 | Nanaumi |
| 2015/0182121 A1 | 7/2015 | Barbour |
| 2015/0238092 A1 | 8/2015 | Masumura |
| 2015/0241342 A1 | 8/2015 | Zhou |
| 2015/0346027 A1 | 12/2015 | Khare |
| 2015/0351635 A1 | 12/2015 | Cerussi |
| 2016/0085135 A1 | 3/2016 | Park |
| 2016/0157723 A1 | 6/2016 | Kanick |
| 2016/0216503 A1 | 7/2016 | Kim et al. |
| 2016/0262723 A1 | 9/2016 | Zhu |
| 2016/0317020 A1* | 11/2016 | Liu ..................... G01B 9/02045 |
| 2016/0363527 A1 | 12/2016 | Ruan |
| 2017/0036275 A1* | 2/2017 | Lukac .................. A61C 1/0046 |
| 2017/0118423 A1 | 4/2017 | Zhou |
| 2017/0156605 A1 | 6/2017 | Nakao et al. |
| 2017/0163946 A1 | 6/2017 | Komanduri |
| 2017/0168565 A1 | 6/2017 | Cohen |
| 2017/0202633 A1 | 7/2017 | Ju |
| 2017/0230555 A1 | 8/2017 | Tabirian |
| 2017/0231501 A1 | 8/2017 | Culver |
| 2018/0070891 A1 | 3/2018 | Jepsen |
| 2018/0153420 A1* | 6/2018 | Fine .................... A61B 5/02416 |
| 2018/0249911 A1* | 9/2018 | Hosoda ............... A61B 5/6826 |
| 2019/0008388 A1 | 1/2019 | Ando et al. |
| 2019/0053745 A1 | 2/2019 | Nakaji |
| 2019/0150745 A1 | 5/2019 | Sobek et al. |
| 2020/0022578 A1 | 1/2020 | Ruan et al. |
| 2020/0059611 A1 | 2/2020 | Delgado et al. |
| 2021/0161407 A1* | 6/2021 | Gush .................... A61B 5/7221 |
| 2021/0321887 A1* | 10/2021 | Fukazawa ............. A61B 1/045 |
| 2021/0346711 A1* | 11/2021 | Ansari ..................... A61N 2/02 |

OTHER PUBLICATIONS

Hofmann et al. Differential light detector, Rev. Sci. Instrum, Feb. 1979, vol. 50, No. 2, paes 249-252.

Freund et al. Memory Effects in Propagation of Ooptical Waves through Disordered Media, Physical Review Letters, Nov. 14, 1988, vol. 61, No. 20, pp. 2328-2331.

Goodman et al. Wavefront-Reconstruction Imaging Through Random Media, Jun. 15, 1966, vol. 8, No. 12, pp. 311-313.

Peng et al. Low loss liquid crystals for infrared applications, Liquid Crystal, 2014, vol. 41, No. 11, pp. 1545-1552.

International Searching Authority, Patent Cooperation Treaty, European Application No. PCT/US2021/24984, Notification dated Jun. 29, 2021, 2 pages.

International Searching Authority, Patent Cooperation Treaty, Written Opinion of the International Searching Authority, European Application No. PCT/US2021/24984, Notification dated Jun. 29, 2021, 7 pages.

\* cited by examiner

OPTICAL IMAGING FROM LIGHT COHERENCE

CROSS-REFERENCE TO RELATED APPLICATIONS

This application claims priority to U.S. provisional Application No. 63/016,011 filed on Apr. 27, 2020, which is hereby incorporated by reference.

BACKGROUND INFORMATION

Imaging devices are used in contexts such as healthcare, navigation, and security, among others. Imaging systems often measure radio waves or light waves to facilitate imaging. Imaging that measures light scattered by an object is especially challenging and advances to the devices, systems, and methods to improve optical imaging are sought to increase speed, increase resolution, reduce size and/or reduce cost.

BRIEF DESCRIPTION OF THE DRAWINGS

Non-limiting and non-exhaustive embodiments of the invention are described with reference to the following figures, wherein like reference numerals refer to like parts throughout the various views unless otherwise specified.

DETAILED DESCRIPTION

Figure 1:
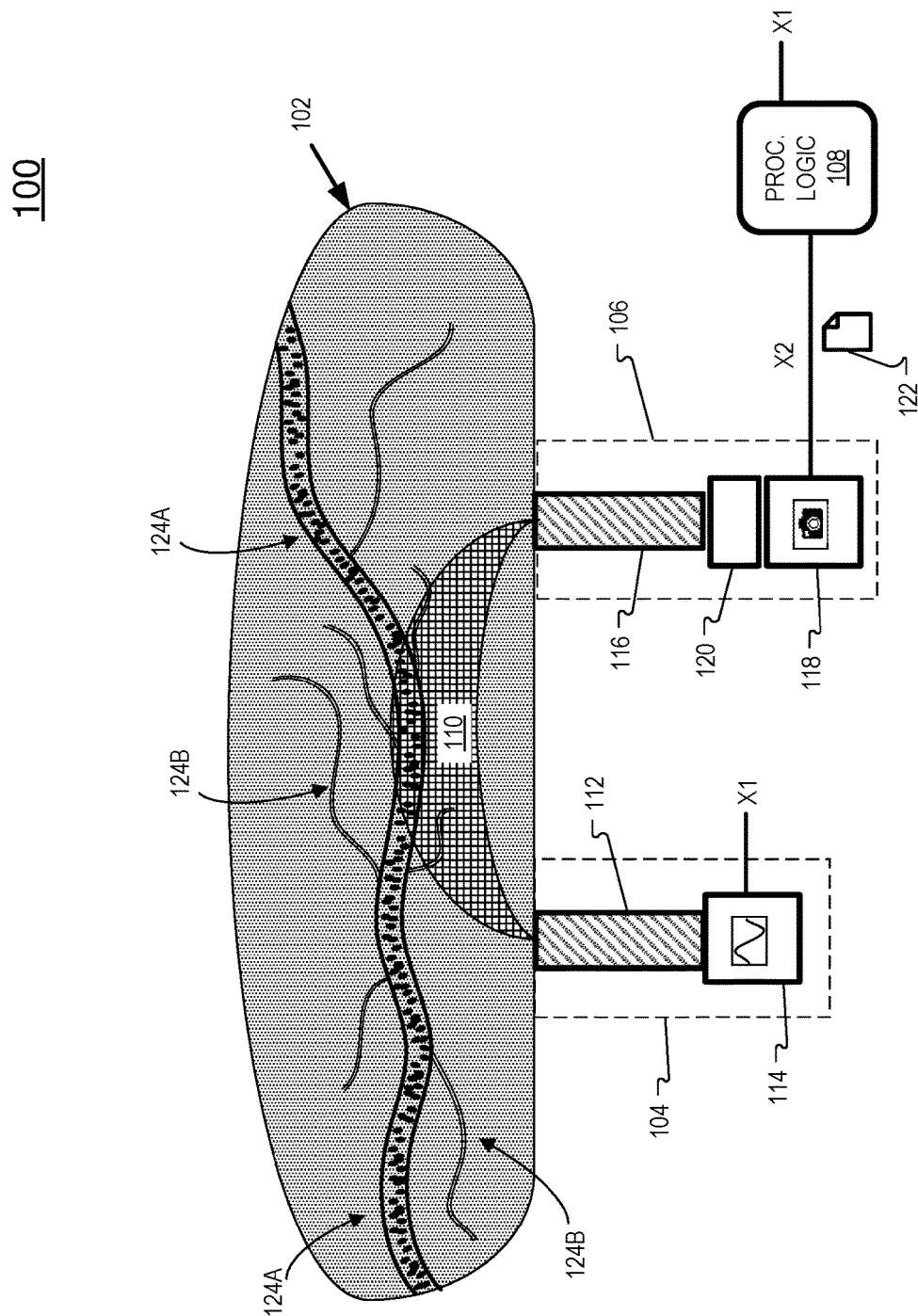
FIG. 1 illustrates an imaging system configured to determine blood characteristics of a tissue sample, in accordance with aspects of the disclosure.

Embodiments of optical imaging with light coherence are described herein. In the following description, numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In aspects of this disclosure, visible light may be defined as having a wavelength range of approximately 380 nm-700 nm. Non-visible light may be defined as light having wavelengths that are outside the visible light range, such as ultraviolet light and infrared light. Infrared light having a wavelength range of approximately 700 nm-1 mm includes near-infrared light. In aspects of this disclosure, near-infrared light may be defined as having a wavelength range of approximately 700 nm-1.4 µm.

This disclosure will generally describe imaging a diffuse medium in the context of human tissue in the medical context. However, the content of this disclosure may be applied to medical imaging, navigation, security, scientific research, or other contexts that image diffuse mediums or objects.

Human tissue is translucent to infrared light, although different parts of the human body (e.g. skin, blood, bone) exhibit different absorption and scattering coefficients. Researchers have attempted to use the properties of infrared light for medical imaging purposes, but size and cost constraints have been prohibitive for wide-scale adoption. Illuminating tissue and other diffuse media with near-infrared light for imaging purposes is sometimes referred to as Diffuse Optical Tomography. In one optical technique, Laser Speckle Imaging can be used to detect light primarily reflected near the surface of a sample, severely lacking depth of measurement. In another Diffuse Optical Tomography technique, Diffuse Correlation Spectroscopy uses an avalanche photodiode to measure coherence by looking at a single speckle over time. However, a single speckle provides limited information on the movement of fluid within a sample.

In contrast to Laser Speckle Imaging and Diffuse Correlation Spectroscopy, some embodiments of this disclosure may include an imaging system that may be configured to emit laser light through a first optical fiber into a tissue sample, detect diffused light from the tissue sample through a second optical fiber, capture an image of the diffused light, and determine blood flow data within the tissue sample at least partially based on coherent light interference patterns in the image. The imaging system may emit laser light using one or more coherent light sources having one or more optical fibers coupled to one or more coherent light sources. The imaging system may detect diffused light using one or more light detectors having one or more optical fibers coupled to one or more image sensors. The imaging system may determine blood characteristics based on the image by using processing logic coupled to the light sources and light detectors.

The processing logic may use coherent light interference represented in the image to determine blood characteristics. Coherent light includes, but is not limited to, light waves or photons having the same frequency, phase, and polarization. Coherent light interference in an image may be manifest or captured as speckles, which include bright and dark spots of one or more pixels in an image. Dark pixels are pixels that have a lower pixel value than surrounding pixels and/or than the average pixel value of an image. Bright pixels are pixels that have a higher pixel value than surrounding pixels and/or than the average pixel value of an image. Quantities of speckles, and therefore coherent light interference, in an image may be detected using the standard deviation of all of the pixels of an image. More specifically, speckle contrast may be determined by dividing the standard deviation of the pixel values of an image by the mean of the pixel values of an image (i.e., std/mean). The speckle contrast of an image is compared to one or more data models that map the speckle contrast to quantities of blood flowing through a tissue sample, in an embodiment. Blood characteristics may include the quantity of blood flowing through an area, the velocity of the blood, and may also include the concentration and oxygenation levels of hemoglobin. Some blood characteristics are blood flow characteristics, and blood flow characteristics may include the quantity of blood flowing through a region of tissue and the velocity of blood flowing through a region of tissue. Some blood characteristics may be independent or less dependent on blood flow, and these blood characteristics may include the concentration and oxygenation levels of hemoglobin.

To improve mapping speckle contrast to blood characteristics (e.g., blood flow characteristics), the image sensor's exposure to coherent light may be manipulated. In one embodiment, a laser provides coherent light in pulses having a duration in the range of 10 µs to 1000 µs (e.g., 10 µs, 20 µs, 40 µs, and/or 80 µs). In one embodiment, the exposure time (e.g., the time between pixel reads) of the image sensor is set to, for example, 10 µs, 20 µs, or some duration in the range of 10 µs to 1000 µs.

Embodiments of the imaging system of this disclosure may include various configurations. The imaging system may include multiple light sources, multiple optical fibers, multiple lasers, continuous wave lasers, pulsed lasers, and/or continuous wave laser light that is modulated or chopped. The imaging system may include direct capture of image data from an optical fiber, or may include optically combined captured light with a reference light source. The imaging system may use speckle contrast, interference with a reference beam, and/or optical attenuation to determine blood characteristics within a tissue sample. Various types of data models may be employed to decipher meaning from an image (e.g., speckle contrast).

These embodiments and others will be described in more detail with reference to FIGS. 1-10.

FIG. 1 illustrates an imaging system 100 that is configured to determine blood characteristics in a tissue sample 102 at least partially based on the coherence of diffuse light captured in an image, in accordance with aspects of the disclosure. The coherence of diffuse light in a captured image is manifest in the image as coherent light interference patterns, or speckles. The coherent light interference (or interference patterns) may be quantified by determining the speckle contrast of an image of the diffuse light exiting tissue sample 102. The speckle contrast values may be correlated or mapped to blood flow rates and other blood characteristics. The speckle contrast values may therefore be used to identify blood vessel occlusions, which may be indicative of health issues. Imaging system 100 may include a light source 104, a light detector 106, and processing logic 108 that are configured to measure blood characteristics in tissue sample 102. Various features of imaging system 100 are described in further detail below.

Light source 104 is configured to emit light 110 into tissue sample 102. Light source 104 includes a source optical fiber 112 and a light generator 114 coupled to source optical fiber 112. Source optical fiber 112 is positioned against tissue sample 102 to provide a path for photons to travel between light generator 114 and tissue sample 102. Light generator 114 is configured to generate coherent light of a narrow band of frequencies. Light generator 114 may be a laser source configured to emit near-infrared laser light. In one embodiment, the near-infrared laser light has a wavelength between 700 nm and 1000 nm. In one embodiment, the laser light has a wavelength of 600 nm to 900 nm. The laser light may provide a narrow band of coherent light at approximately 850 nm, for example. The laser may be a continuous wave (CW) laser. The output of the laser may be pulsed, chopped, or modulated to provide pulses of coherent light. The pulses may have a duration of 10 µs, 20 µs, or some other duration from 10 µs to 1000 µs, according to various implementations.

Light detector 106 is configured to detect coherent light from measurement beam 110, which is formed from the coherent light diffused into tissue sample 102 by light source 104. Light detector 106 may include a detector optical fiber 116 coupled to an image sensor 118. Detector optical fiber 116 may be a multi-mode optical fiber having a core diameter of 50 µm, 60 µm, or some diameter greater than approximately 10 µm. Source optical fiber 112 may be a single-mode optical fiber having a diameter of 9 µm or less.

Detector optical fiber 116 captures diffused light (i.e., an exit signal) from tissue sample 102 and transmits the diffused light from the measurement beam 110 to image sensor 118. Image sensor 118 may be a complementary metal oxide semiconductor ("CMOS") image sensor or a charge-coupled device ("CCD") image sensor. Image sensor 118 includes an array of pixels that are each responsive to photons received from measurement beam 110 through detector optical fiber 116. Pixels in image sensor 118 respond to interference of coherent light with dark pixels values and bright pixels values that manifest in an image as speckles. Speckle contrast is then used to determine blood characteristics of blood vessels within tissue sample 102. In one embodiment, image sensor 118 has image sensor pixels having a pixel pitch of one micron or less. The pixel resolution of image sensor 118 may vary depending on the application. In one embodiment, image sensor 118 is 1920 pixels by 1080 pixels. In one embodiment, image sensor 118 is a 40 megapixel or greater image sensor.

In an embodiment, a light converter 120 is positioned between detector optical fiber 116 and image sensor 118 to facilitate transmission of light between light detection optical fiber 116 and the image sensor 118. Light converter 120 may be implemented as one or more of a lens, a filter, and an optical switch, in an embodiment. Light converter 120 may include a bandpass filter. Light converter 120 may be a high pass filter that filters out ambient light wavelengths.

Processing logic 108 is coupled to light source 104 and light detector 106 to support operation of the imaging system 100, according to an embodiment. Processing logic 108 uses channel X1 to send control signals to light source 104 to operate light source 104. Examples of operating light source 104 include turning light generator 114 on and off and include chopping the output of light generator 114.

Processing logic 108 uses channel X2 to send control signals to image sensor 118, in an embodiment. Processing logic 108 may configure the exposure time of the image sensor 118. Examples of the exposure time include 10 μs, 20 μs, 30 μs, or various increments in the range of 10 μs to 1000 μs. The strength of the speckle contrast signal may decrease with increasing exposure times, e.g., greater than 100 μs. Therefore, in some implementations, exposure time for image sensor 118 is configured to be less than 100 μs.

Processing logic 108 uses channel X2 to receive image data 122 from image sensor 118, in an embodiment. The image data 122 may include an array of pixel values representing exposure of the pixel array of image sensor 118 to photons from measurement beam 110. Measurement beam 110 is the portion of light emitted by light source 104 that exits into light detector 106. The portion of measurement beam 110 that exits tissue sample 102 into light detector 106 may be referred to as an exit signal. When light source 104 is a laser, measurement beam 110 includes laser light emitted by light source 104 into light tissue sample 102 that at least partially propagates to light detector 106. The diffused light of measurement beam 110 may take a more round-about optical path than is illustrated in FIG. 1. Processing logic 108 may use channel X2 to receive image data 122 for speckle contrast analysis.

Processing logic 108 is configured to perform speckle contrast analysis on image data 122 to identify blood characteristics within tissue sample 102, in an embodiment. Processing logic 108 may perform speckle contrast analysis on image data 122 by calculating the standard deviation of the pixels of an image, calculating the mean of the pixels of the image, and identifying a speckle contrast value as the standard deviation divided by the mean of the pixels of the image.

Speckle contrast may be used to provide blood characteristics in tissue sample 102. Speckle contrast values vary based on blood volume passing through blood vessels 124. Blood vessels 124 may include larger blood vessels 124A and smaller blood vessels 124B. Larger blood vessels 124A may include arterioles, metarterioles, thoroughfare channels, and venules. Smaller blood vessels 124B may include capillaries. Smaller blood vessels 124B may contribute more significantly to speckle contrast values than larger blood vessels 124A. Speckle contrast may be mapped or modeled to be inversely proportional to blood volume passing through blood vessels 124. Speckle contrast decreases with increases in blood volume passing through blood vessels 124. Speckle contrast increases with decreases in blood volume passing through blood vessels 124. Speckle contrast values may be compared to modeled blood characteristics to identify decreases in blood flow volume (e.g., caused by blood clots or other vascular occlusions) passing through blood vessels 124. As a result, it may be possible to characterize health issues associated with decreases in blood volume in portions of a body (e.g., within the brain).

Processing logic 108 compares speckle contrast values to data models that are associated with blood characteristics for tissue sample 102. Data models may vary based on the type of tissue sample 102 and/or based on characteristics of the test subject. Blood characteristics within tissue sample 102 may differ for various parts of the body (e.g., arm, leg, breast, brain, prostate, heart, etc.). Blood characteristics within tissue sample 102 may differ based on characteristics of a test subject (e.g., body mass index "BMI", gender, age, height, fitness level, genetics, health, etc.). Accordingly, processing logic 108 may receive characteristics of a test subject, and compare speckle contrast values against one or more particular data models (from a plurality of data models), to determine blood characteristics from the measured and/or calculated speckle contrast values. Processing logic 108 may be configured to compare blood characteristics or blood flow characteristics between different locations in tissue sample 102.

Processing logic 108 may be configured to determine blood characteristics using intensity values, according to an embodiment. For example, processing logic 108 may determine an intensity value of image data 122 by calculating a mean of the pixels values of the image data 122. Various intensities may be mapped or correlated with optical attenuation coefficients, which may vary with changes in blood flow.

Figure 2:
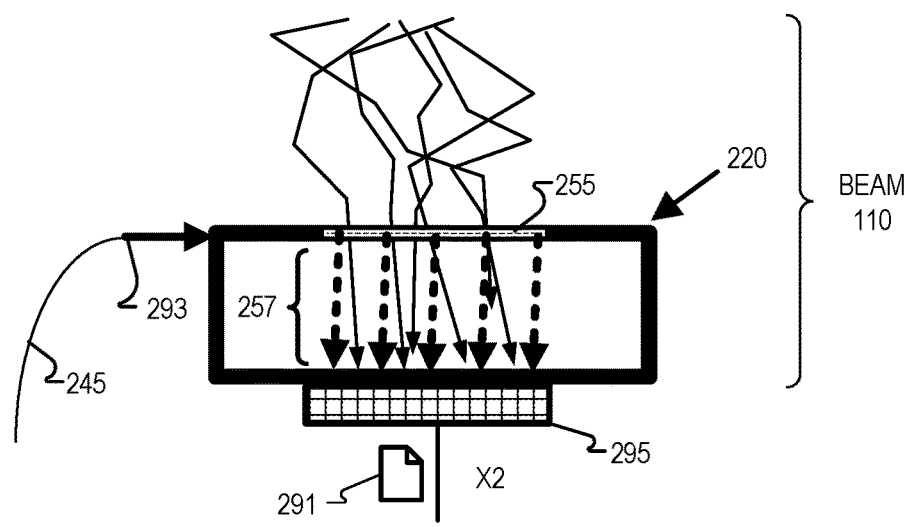
FIG. 2 illustrates an example light detector having an image sensor configured to image an interference pattern generated by a reference beam interfering with a measurement beam, in accordance with aspects of the disclosure.

FIG. 2 illustrates a light detector 220 that is configured to capture coherent light interference patterns to determine blood characteristics, in accordance with aspects of the disclosure. Light detector 220 is an example implementation a portion of light detector 106 (e.g., image sensor 118 and/or light converter 120). Light detector 220 may include an image sensor 295 configured to image an interference pattern generated by a reference beam 257 interfering with measurement beam 110. Light detector 220 is configured to receive measurement beam 110. Reference beam 257 is the same wavelength as laser light emitted by light generator 114 of light source 104, in some embodiments. Reference beam 257 may be provided to an optical input 293 of light detector 220 by an optical fiber 245 that receives (for example) laser light from light generator 114, to ensure the wavelength of reference beam 257 is the same as the wavelength of measurement beam 110. In the illustration of FIG. 2, a reference optical element 255 is configured to direct reference beam 257 to illuminate image sensor 295. Reference optical element 255 may include a surface relief grating, Bragg grating, and/or a holographic optical element coupled to receive the reference beam from optical input 293 and direct reference beam 257 to image sensor 295. In some embodiments, reference optical element 255 is configured to direct reference beam 257 to become incident upon the image sensor 295 at an angle slightly offset from an angle that is perpendicular to an imaging plane of the image sensor 295.

Light detector 220 is configured to capture image data 291 of the interference pattern generated by measurement beam 110 interfering with reference beam 257. Processing logic 108 (shown in FIG. 1) may be configured to initiate the image capture by image sensor 295 via communication channel X2. The intensity of the interference pattern captured by the image sensor 295 of light detector 220 can be analyzed using techniques disclosed herein to determine blood characteristics (e.g., blood flow rates, hemoglobin oxygenation levels, etc.). For example, the interference pattern from diffuse light and a reference beam may include fringes in image data 291, and the contrast between fringe patterns in image data 291 may be used to determine blood characteristics (e.g., blood flow characteristics).

Figure 3:
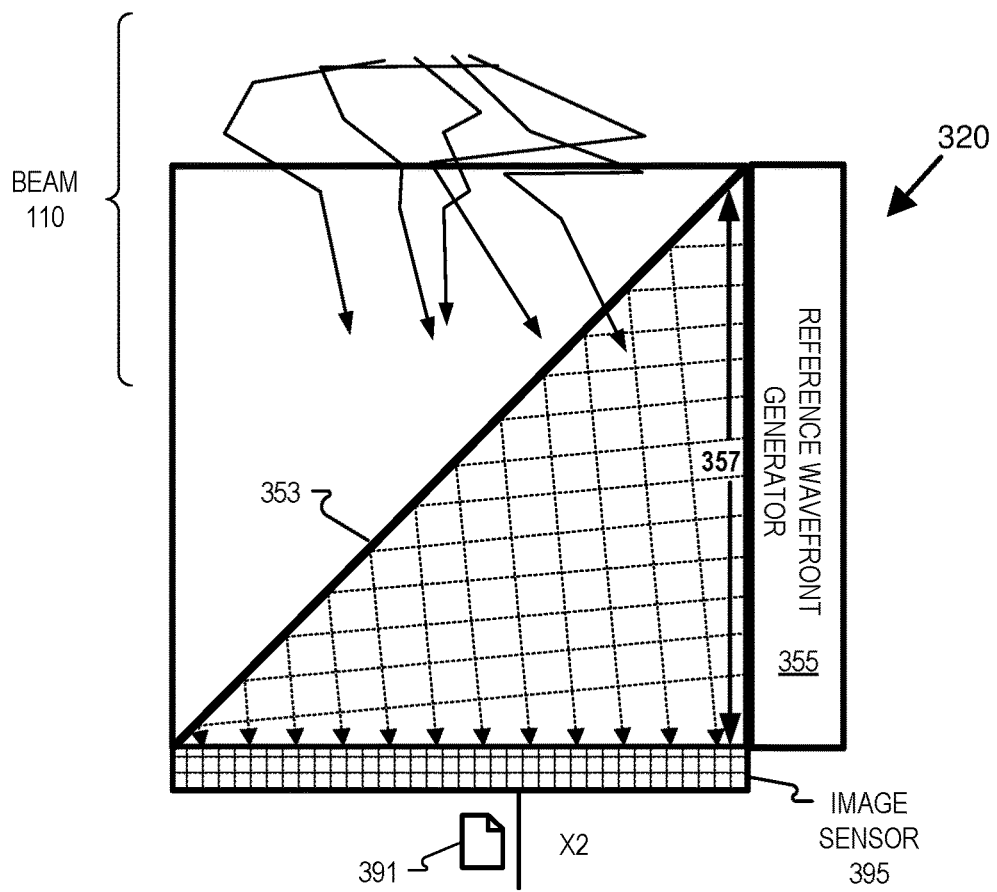
FIG. 3 illustrates an example configuration of a light detector including a beam splitter, in accordance with aspects of the disclosure.

FIG. 3 illustrates a light detector 320 that is configured to capture coherent light interference patterns to determine blood characteristics in a tissue sample, in accordance with aspects of the disclosure. Light detector 320 is an example implementation of light detector 106 (shown in FIG. 1). Light detector 320 is configured to receive measurement beam 110. Light detector 320 includes an image sensor 395 configured to capture image data 391 of an interference between measurement beam 110 and reference beam 357. At least a portion of measurement beam 110 propagates through beam splitter 353 to interfere with the portion of reference beam 357 that is reflected back toward image sensor 395.

Therefore, image data 391 generated by image sensor 395 is representative of an interference of reference beam 357 with measurement beam 110.

Reference wavefront generator 355 generates reference beam 357, which may be a near-infrared reference beam or a visible light reference beam. Reference wavefront generator 355 may include one or more lasers and corresponding optics to generate a substantially uniform wavefront for reference beam 357. Reference wavefront generator 355 may receive light from a same light generator (e.g., light generator 114 shown in FIG. 1) that provides light for light source 104, in some embodiments. Reference beam 357 may be the same wavelength as the light emitted from light source 104. Or, reference beam 357 may be the same wavelength as (doppler) wavelength shifted portion of measurement beam 110, in some implementations.

In one embodiment, reference wavefront generator 355 is disposed to effect delivery of the reference beam 357 to image sensor 395 at an angle to a pixel plane of the image sensor 395. Image sensor 395 may include image pixels disposed in two-dimensional rows and columns that define the pixel plane of the image sensor 395. Processing logic 108 may be configured to initiate the image capture by image sensor 395 via communication channel X2.

FIGS. 4A, 4B, 4C, and 4D illustrate graphical representations of blood characteristics that may be incorporated into one or more data models to determine a blood flow index and/or blood flow rates from coherent light interference patterns, in accordance with embodiments of the disclosure.

Figure 4A:
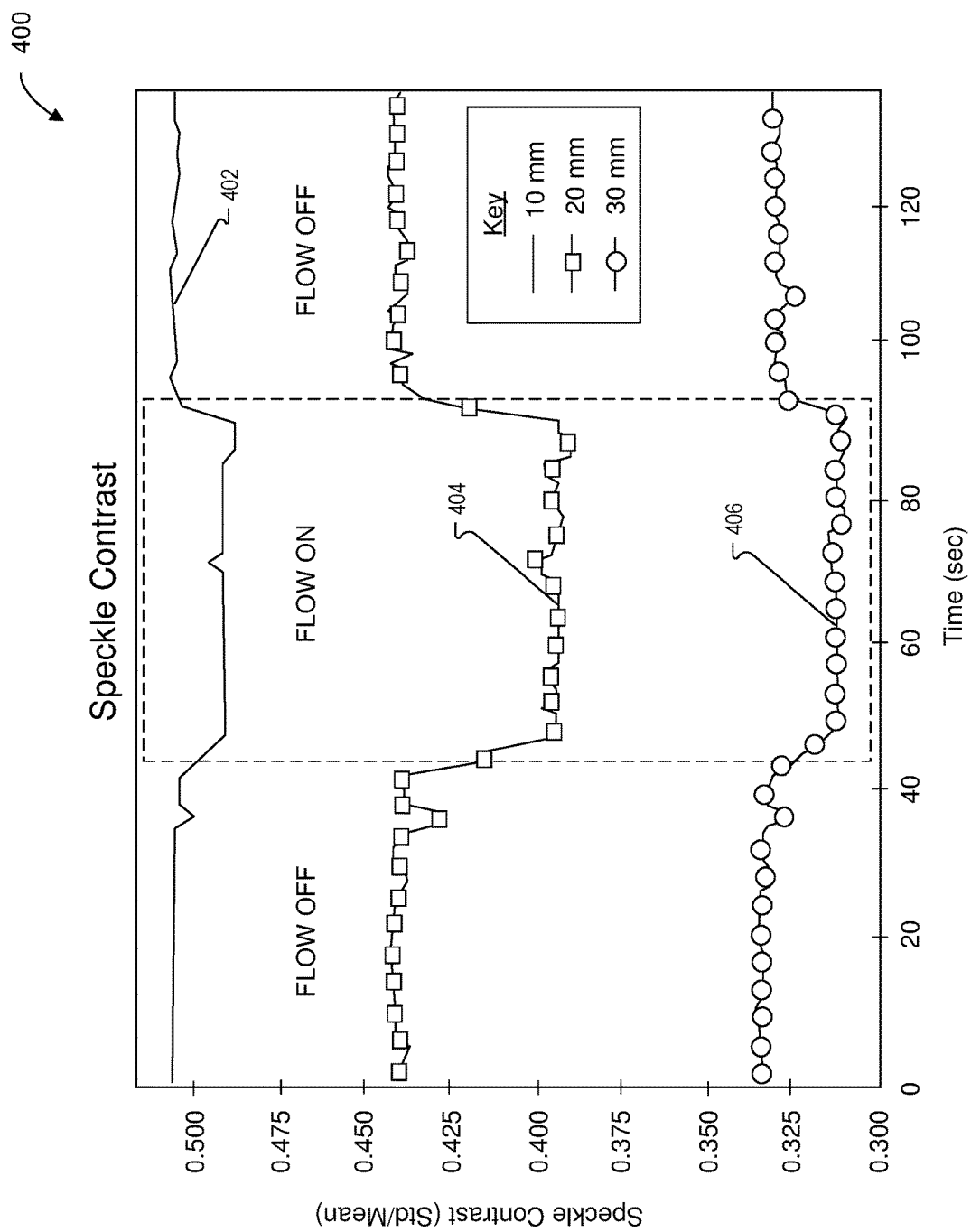
FIGS. 4A-4D illustrate example graphs of blood characteristics that may be incorporated into data models, in accordance with aspects of the disclosure.

FIG. 4A illustrates a speckle contrast graph 400 that demonstrates how speckle contrast values for image data (e.g., image data 122 of FIG. 1, image data 291 of FIG. 2, image data 391 of FIG. 3, etc.) may vary based on blood characteristics, in accordance with embodiments of the disclosure. Speckle contrast graph 400 includes an x-axis and a y-axis. The x-axis includes time in seconds, and the y-axis includes speckle contrast values, which may be defined as the standard deviation of (e.g., all or a sub-section of) pixel values of an image divided by the mean of (e.g., all or a sub-section of) pixel values of the image. Speckle contrast graph 400 includes a data line 402 that shows an example of speckle contrast values varying with respect to time when blood flow (or simulated blood flow) is at least partially constricted, released, and at least partially constricted. Data line 402 represents measurements captured by a light detector positioned 10 mm from a light source. Data line 404 is similar to data line 402, but data line 404 represents measurements captured by a light detector positioned 20 mm from a light source. Data line 406 is similar to data line 402, but data line 406 represents measurements captured by a light detector positioned 30 mm from a light source. Speckle contrast values decrease when blood flow increases, while tissue is illuminated with light having wavelengths in the range of approximately 600 nm to 1000 nm, according to embodiments of the disclosure. Notably, speckle contrast values vary with changes in distance between a light source and a light detector, and the speckle contrast values vary with changes in exposure time of the tissue sample to coherent light.

Figure 4B:
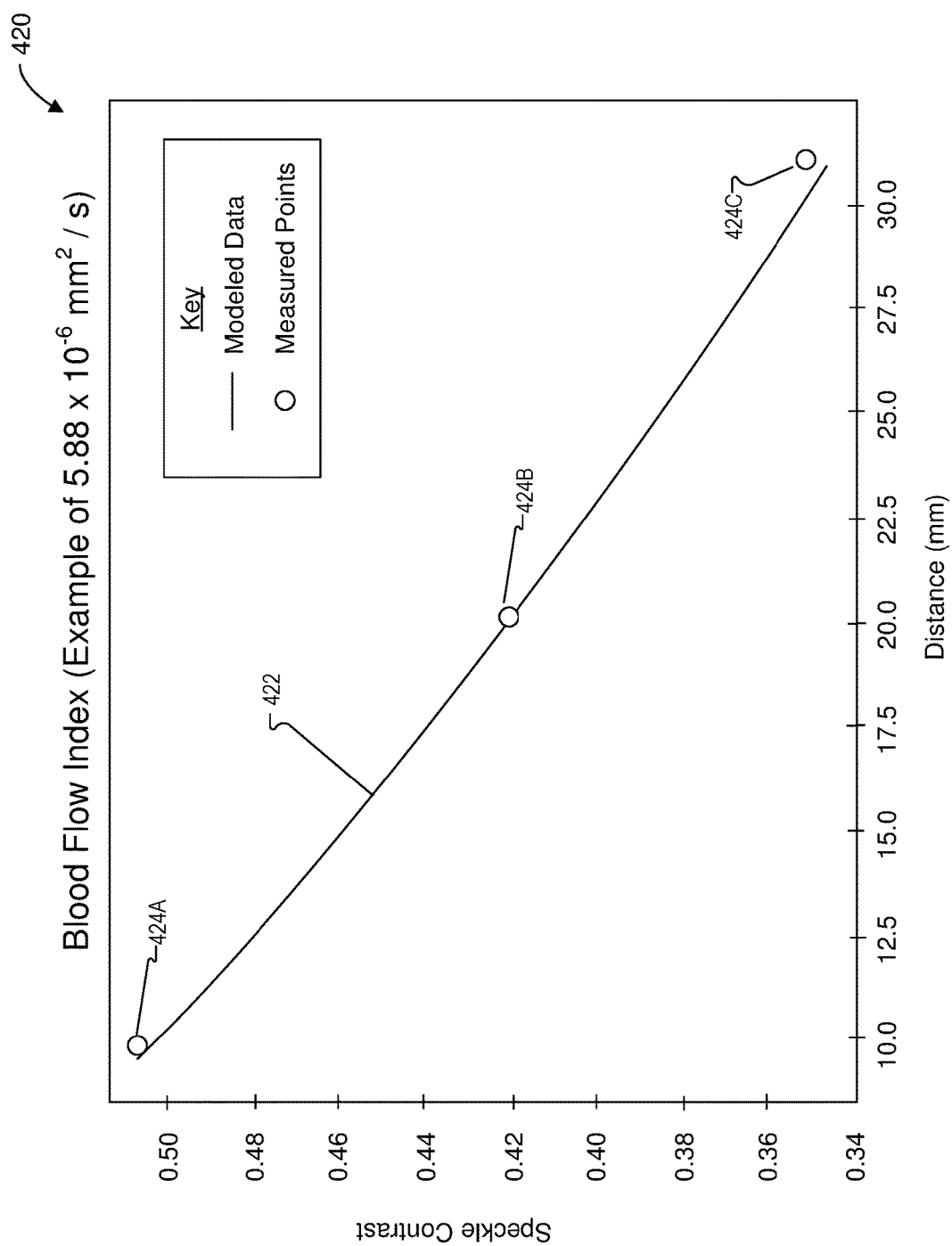

FIG. 4B illustrates a blood flow index graph 420 that demonstrates how a data model may map speckle contrast values against distance for a particular blood flow index value, in accordance with embodiments of the disclosure. Blood flow index graph 420 includes an x-axis and a y-axis. The x-axis includes distance between a light source and light detector in millimeters, and the y-axis includes speckle contrast values. Blood flow index graph 420 includes a data line 422 that models illustrative speckle contrast values, as they change with distance between a light source and a light detector. Data line 422 is an example of values that may be modeled for a particular blood flow index, e.g., $5.88 \times 10^{-6}$ mm$^2$/s. Data points 424A, 424B, and 424C represent test measurements made at 10 mm, 20 mm, and 30 mm that fit relatively well to an example data model. The data line 422 is non-linear, indicating that a non-linear relationship exists between speckle contrast values and distance between source and detector optical fibers, according to an embodiment.

Figure 4C:
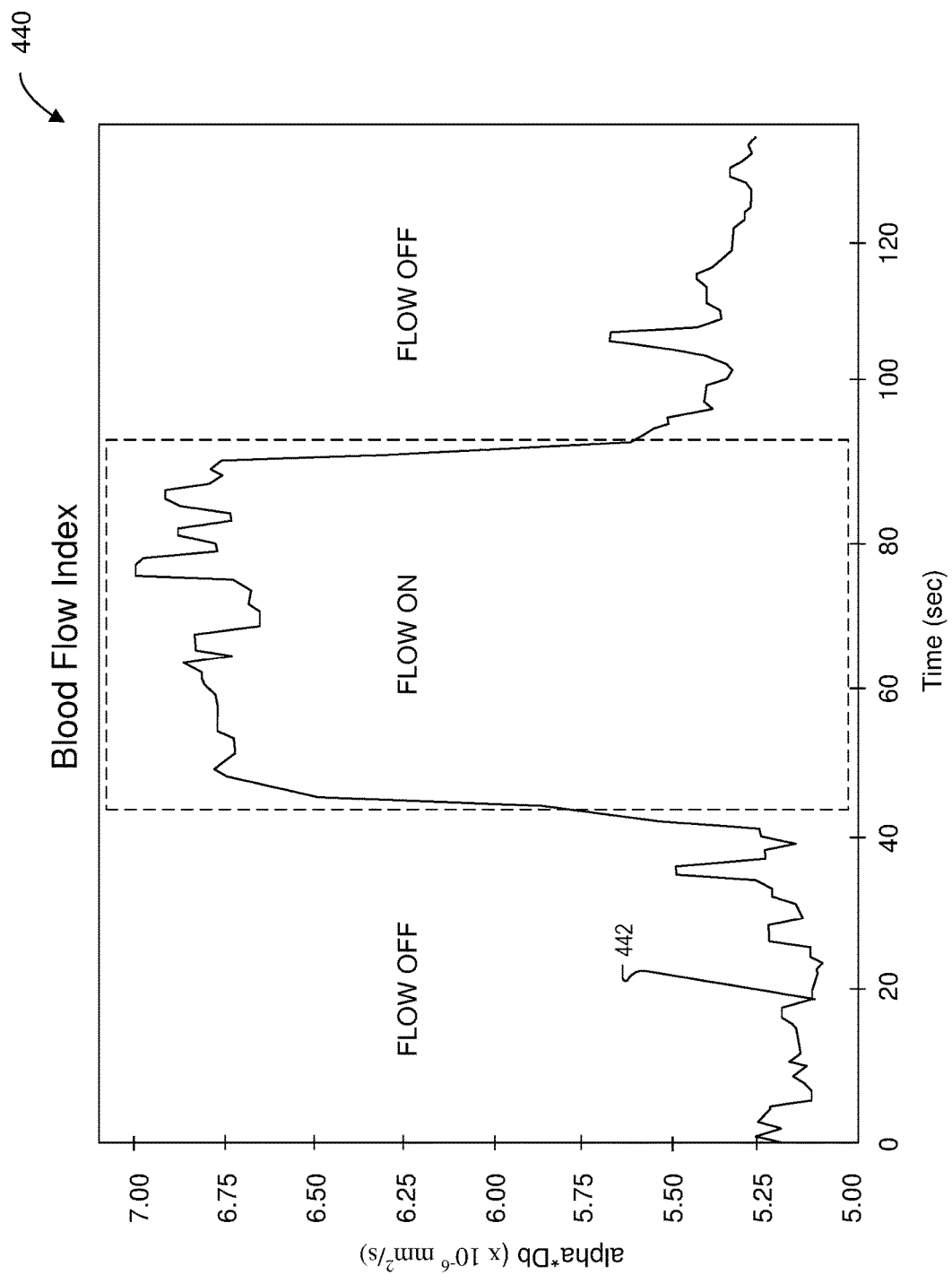

FIG. 4C illustrates a blood flow index graph 440 that demonstrates how blood flow index values may vary based on blood characteristics, with respect to time, in accordance with embodiments of the disclosure. Blood flow index graph 440 includes an x-axis and a y-axis. The x-axis includes time in seconds, and the y-axis includes blood flow index values in squared millimeters per seconds (mm$^2$/s). The blood flow index values represent a quantity of blood flowing through a two-dimensional cross-section per second, without regard to the diameter of the blood vessel. The blood flow index may be determined by multiplying a fraction of scatterers that are moving (e.g., blood cells and/or hemoglobin) by a diffusion coefficient of the scatterers. The fraction of scatterers that are moving are represented as "alpha", and the diffusion coefficient of the scatterers is represented as "Db" in the y-axis descriptor. The diffusion coefficient may be an effective Brownian diffusion coefficient used to model scatterers undergoing Brownian motion. Blood flow index graph 440 includes a data line 442 that illustrates an increase in blood flow, for example, from $5.25 \times 10^{-6}$ mm$^2$/s to $6.75 \times 10^{-6}$ mm$^2$/s, in response to de-constricting blood vessels (e.g., at time 40 s). Blood flow index graph 440 includes a data line 442 that illustrates a decrease in blood flow index, for example, from $6.75 \times 10^{-6}$ mm$^2$/s to $5.4 \times 10^{-6}$ mm$^2$/s, in response to constricting blood vessels (e.g., at time 90 s).

Figure 4D:
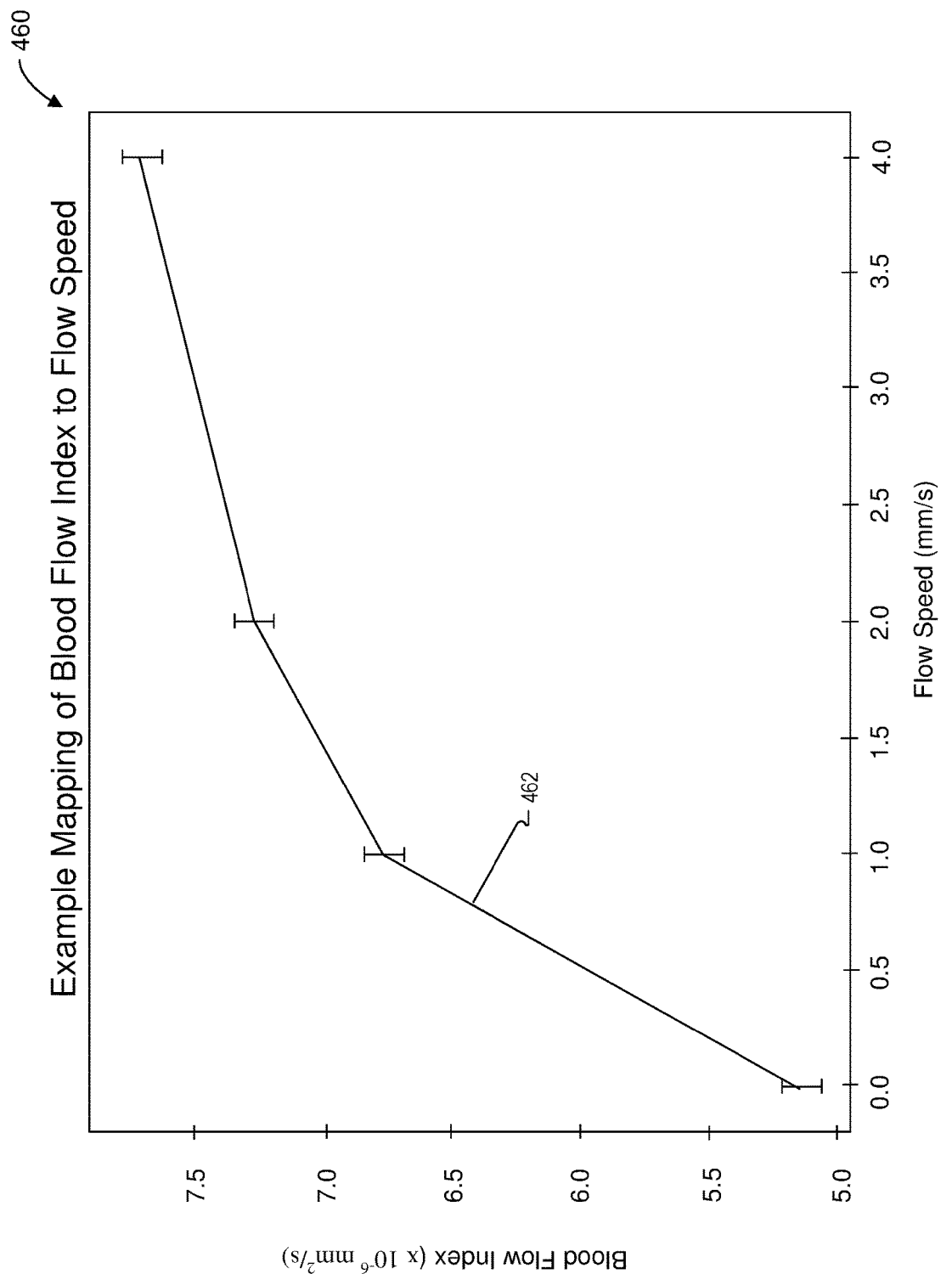

FIG. 4D illustrates a blood flow index graph 460 that demonstrates how a data model may map blood flow index values against blood flow speeds, in accordance with embodiments of the disclosure. The x-axis includes blood flow speeds in millimeters per second. The y-axis includes blood flow index values in squared millimeters per second, scaled by $10^{-6}$ (i.e., $10^{-6}$ mm$^2$/s). Blood flow index graph 460 includes a data line 462 that shows an example of a data that models a map of blood flow index values against blood flow speed. Data line 462 may model measurements of a 4 mm diameter blood vessel located approximately 15 mm from the skin surface, as an example. Blood flow index graph 460 and that graphs of FIGS. 4A-4C are illustrative examples of what data may look like and are merely representative of how speckle contrast may be modeled and how speckle contrast values may be representative of various blood characteristics.

Other blood characteristics may be modeled, measured, and used to obtain information about blood flow within a tissue sample. For example, the mean value of an image may be determined for each image to quantify an intensity of an image. The intensity of captured images may be used to generate a data model of intensity versus distance between a light source and a light detector (e.g., in millimeters). The data model may be built to include values for a variety of optical attenuation coefficients, which may be represented as $\mu$ or $\mu\_eff$. The units of an optical attenuation coefficient ($\mu\_eff$) may be mm$^{-1}$ or per millimeter. The optical attenuation coefficient may be captured over time and may have different values when blood flow is constricted (e.g., via a clot or other occlusion) versus free flowing. In an embodiment, optical attenuation coefficient is determined to classify blood characteristics in a tissue sample.

Figure 5A:
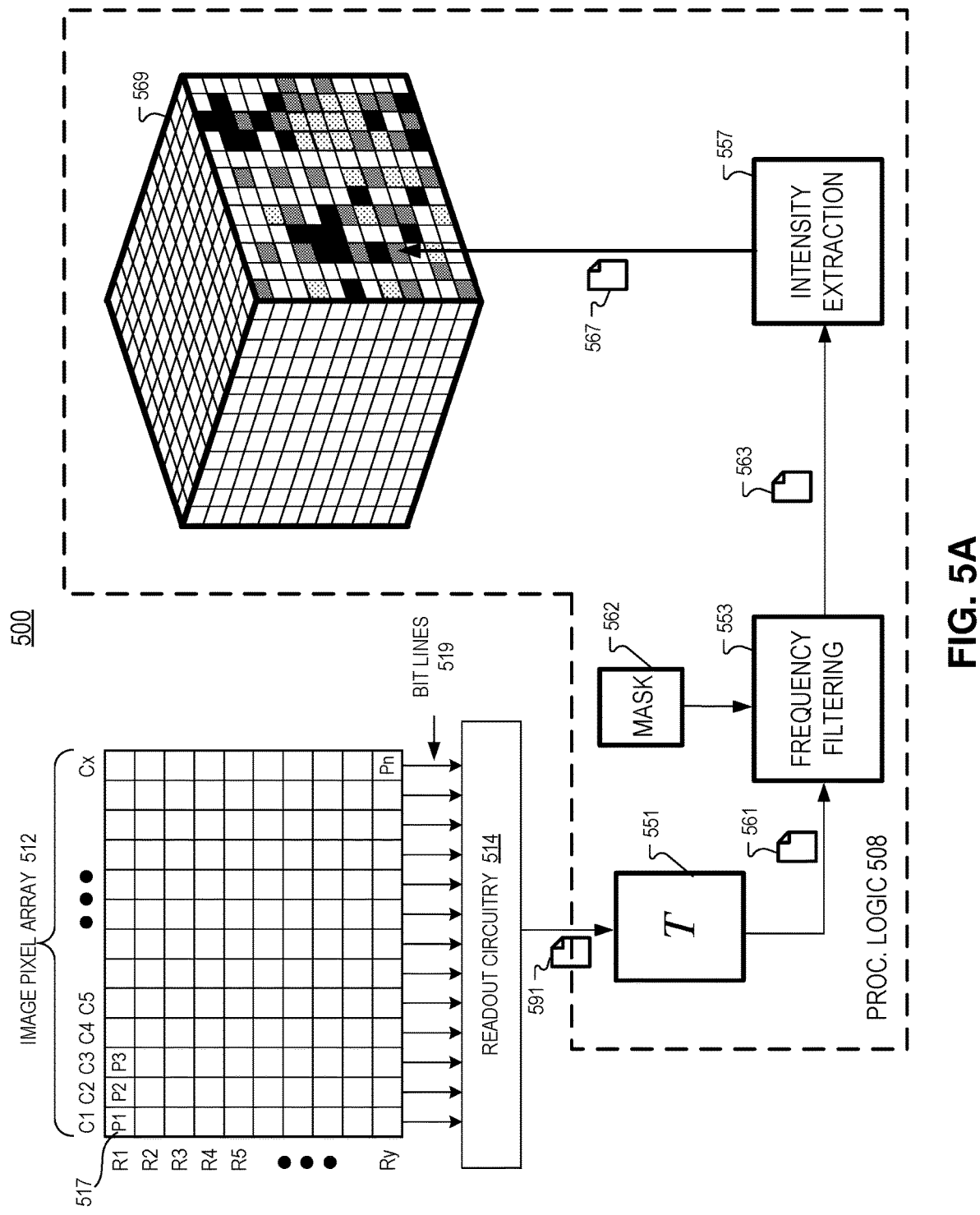
FIGS. 5A-5B illustrate an image pixel array coupled to processing logic configured to generate composite images, in accordance with aspects of the disclosure.

FIG. 5A illustrates a processing logic system 500 that may be an implementation of processing logic (e.g., processing logic 108 of FIG. 1) to process image data (e.g., image data 291 of FIG. 2, image data 391 of FIG. 3, etc.) from an image sensor (e.g., image sensor 295 of FIG. 2, image data 395 of FIG. 3, etc.), in accordance with an embodiment of the disclosure. Processing logic system 500 includes an image pixel array 512 coupled to processing logic 508. Image pixel array 512 represents a pixel array that may be included in an image sensor (e.g., image sensor 118, 295, 395). Processing logic 508 includes features that may be included in processing logic 108, according to an embodiment of the disclosure. Image pixel array 512 includes image pixels 517 arranged in integer number x columns (C1-Cx) and integer number y rows (R1-Ry). Readout circuitry 514 is coupled to read the signal value from each image pixel 517 via bitlines 519. Transform engine 551 in processing logic 508 is coupled to receive the image 591 from readout circuitry 514. Image 591 may be an example of image data 122. Transform engine 551 generates a frequency domain image 561 by performing a Transform operation on image 591 received from readout circuitry 514. In one embodiment, the Transform operation includes an inverse Fourier transform. In one embodiment, the Transform operation includes a discrete cosine transform.

Frequency filtering engine 553 is coupled to receive the frequency domain image 561 from Transform engine 551 and also coupled to receive mask 562. Frequency filtering engine 553 is configured to multiply the frequency domain image 561 with the mask 562 to generate a filtered frequency domain image 563, in the illustrated embodiment of FIG. 5A. Mask 562 is designed to isolate the interference signal between the sample and reference light beams. Mask 562 may include a matrix that includes '1' values for the portion of the frequency domain image 561 that corresponds to the interference of measurement beam 110 with the reference beam, and '0' values for background signal in the frequency domain image 561. In one embodiment, mask 562 is a two-dimensional Gaussian filter.

Intensity extraction engine 557 is coupled to receive the filtered frequency domain image 563 and configured to extract intensity data 567 from the filtered frequency domain image 563. In one embodiment, generating the intensity data 567 includes averaging intensity values of the filtered frequency domain image 563. In an embodiment where a Fourier transform is used as the transform operation in Transform engine 551, the Fourier coefficients are extracted from filtered frequency domain image 563 and a sum of the logarithm of the absolute value of the Fourier coefficients is calculated. The sum is then used as intensity data 567. In some implementations, intensity extraction engine 557 may compare the sum of the logarithm of the absolute value of the Fourier coefficients to a baseline interference pattern in a baseline image of measurement beam 110 incident on image pixel array 512 that is captured without a tissue sample present to generate intensity data 567. In an embodiment, a baseline intensity value is subtracted from the sum of the logarithm of the absolute value of the Fourier coefficients of filtered frequency domain image 563 to generate intensity data 567 as a voxel value of composite image 569 for a particular measurement.

Processing logic 508 incorporates the intensity data 567 as a voxel value in a composite image 569. Composite image 569 is illustrated as a three-dimensional image in FIG. 5A and may be a three-dimensional image of a diffuse medium such as tissue sample 102 (shown in FIG. 1). In one embodiment, an imaging system (e.g., image system 100 of FIG. 1, imaging system 600 of FIG. 6, etc.) may employ a network of light sources and light detectors to gather blood characteristics from various locations and depths of tissue sample to generate a 3D composite image of a diffuse medium or tissue sample by generating a plurality of image data that correspond to the different voxels of the tissue sample.

Figure 5B:
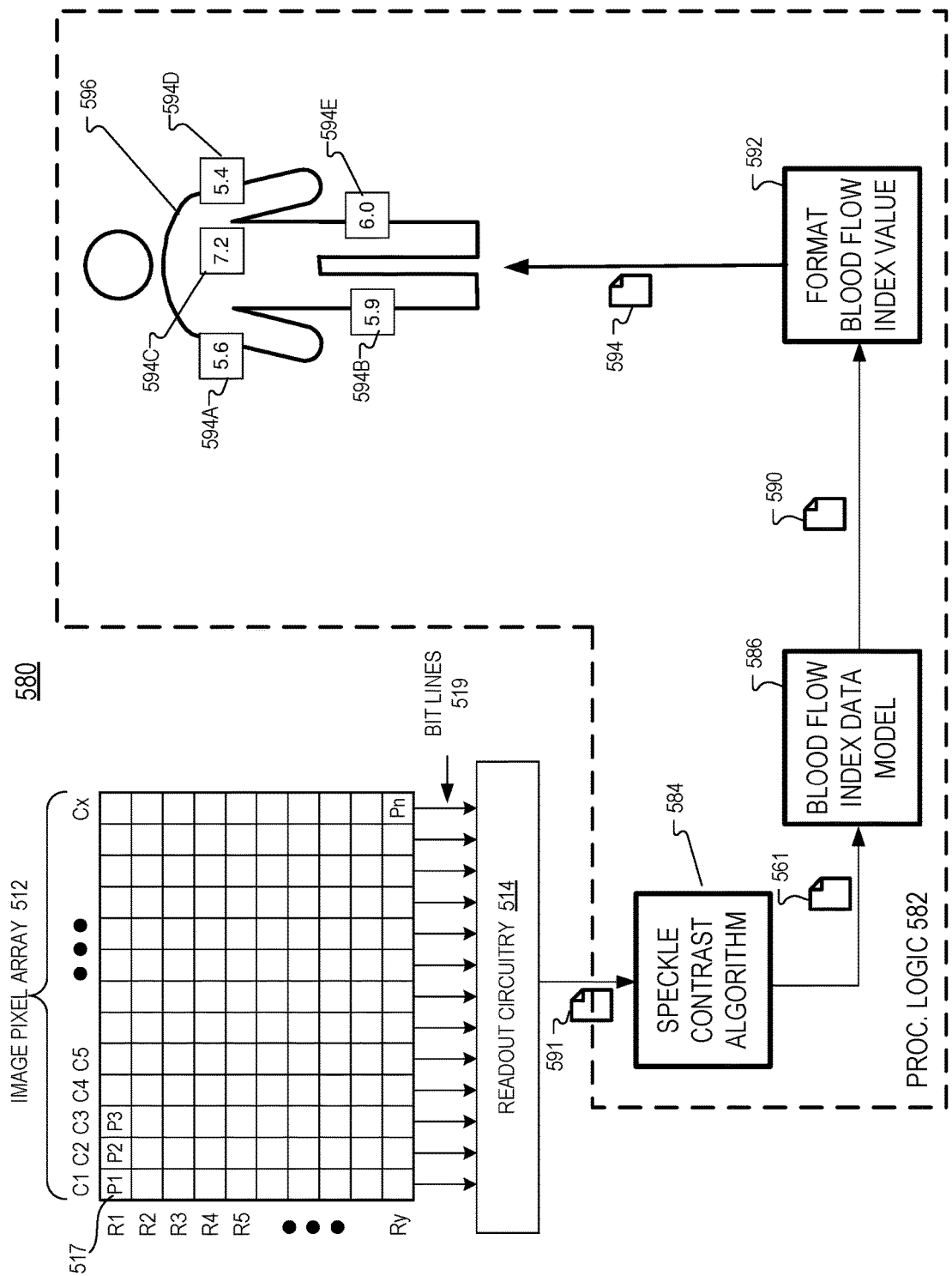

FIG. 5B illustrates a processing logic system 580 that may be an implementation of processing logic 108 (shown in FIG. 1), to process image data from an image sensor (e.g., image sensor 118 of FIG. 1), in accordance with an embodiment of the disclosure. Processing logic system 580 includes image pixel array 512 (shown in FIG. 5A) coupled to processing logic 582. Processing logic 582 includes features that may be included in processing logic 108, to determine blood flow index values from coherent light interference patterns, according to an embodiment of the disclosure.

Processing logic 582 may include a speckle contrast algorithm 584 and a blood flow index data model 586 for determining blood characteristics from an image 591, according to an embodiment of the disclosure. The speckle contrast algorithm 584 is configured to determine the standard deviation of pixel values and determine the mean of the pixel values. The speckle contrast algorithm 584 may generate a speckle contrast value 588 by dividing the standard deviation by the mean of the pixel values. A number of factors may be incorporated into the speckle contrast calculation, including, normalized electric field auto-correlation function, Gaussian moment theorem, pixel size, polarization purity, exposure time, power spectral density, and light bandwidth. Processing logic 582 may apply a speckle contrast value to blood flow index data model 586 to determine a blood flow index value 590. Processing logic 582 may include an operation 592 to format blood flow index value as formatted blood flow index value 594. Processing logic 582 may then display a number of formatted blood flow index values 594A-E (collectively, formatted blood flow index value(s) 594) on a (2D or 3D) composite image 596 of a body or body part to facilitate comprehension of blood flow properties of various tissue samples of a test subject, for example.

Figure 6:
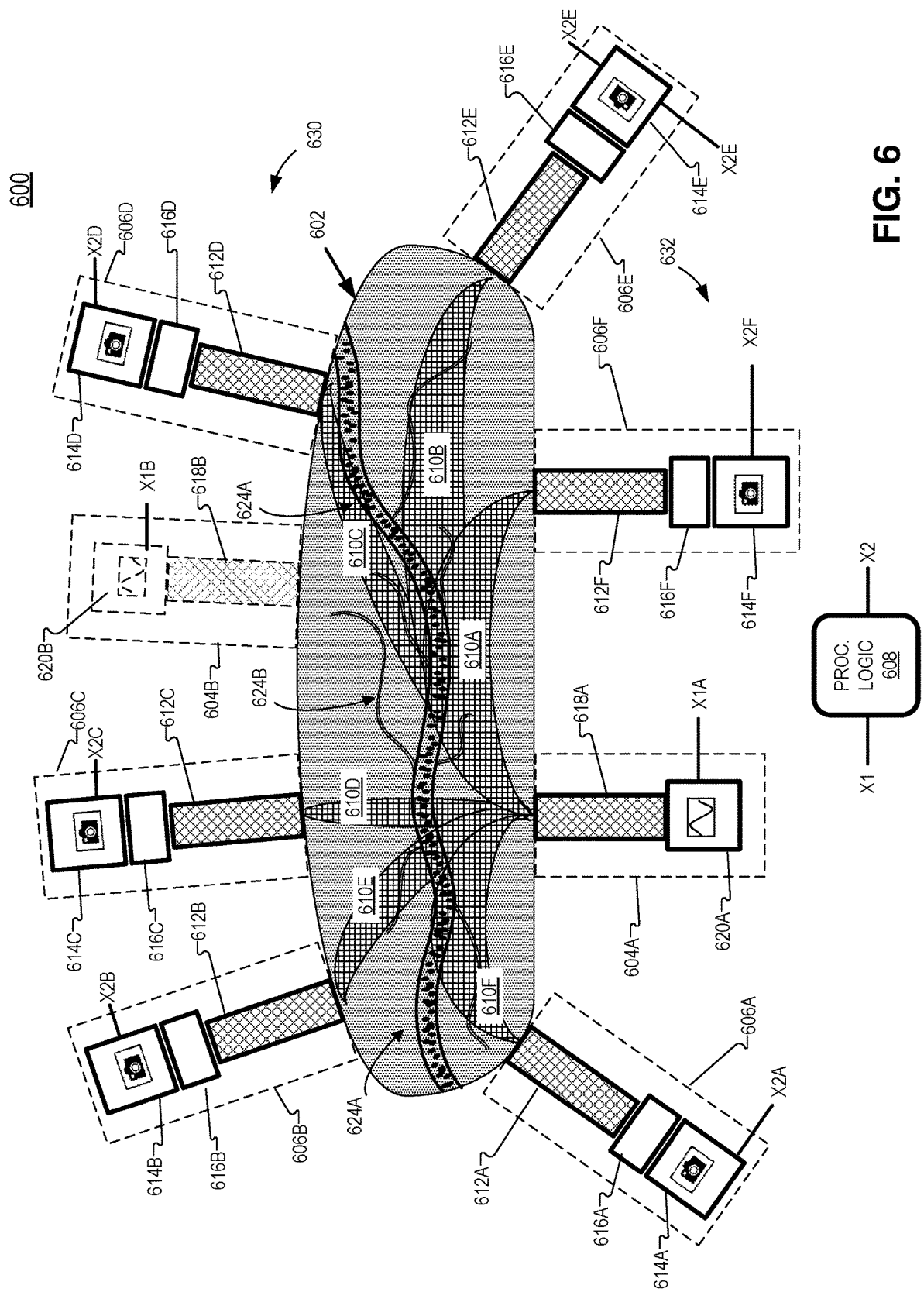
FIG. 6 illustrates an imaging system including a network of light detectors configured to determine blood characteristics, in accordance with aspects of the disclosure.

FIG. 6 illustrates an imaging system 600 that includes a network of light detectors and light sources to perform comparative blood flow analysis and/or to generate data for composite images (e.g., images 569 and 596 of FIGS. 5A and 5B), in accordance with embodiments of the disclosure. Imaging system 600 is applied to a tissue sample 602 and includes a number of light sources 604 (individually, light sources 604A and 604B), a number of light detectors 606 (individually, light detectors 606A, 606B, 606C, 606D, 606E, 606F), and processing logic 608. Tissue sample 602 may include the features of tissue sample 102 of FIG. 1, each of light sources 604 may include the features of light source 104 of FIG. 1, each of light detectors 606 may include the features of light detector 106 of FIG. 1, and processing logic 608 may include the features of processing logic 108 of FIG. 1, in an embodiment.

As illustrated, imaging system 600 may have light detectors 606 distributed in various locations around tissue sample 602 to determine blood characteristics from a variety of locations within tissue sample 602. Each of light detectors 606 may be controlled by and communicate with processing logic 608 over communications channels X2A-F (collectively, communications channels X2). Light detectors 606 capture light and images of measurement beams 610A-F, for example. Light detectors 606B, 606C, 606D positioned on a first side 630 of tissue sample 602 and light detectors 606A, 606E, 606F positioned on a second side 632 of tissue sample 602 may enable processing logic 608 to perform a comparative analysis of blood characteristics of blood vessels 624 within tissue sample 602. Blood vessels 624 may include larger blood vessels 624A (e.g., arterioles, metarterioles, thoroughfare channels, and venules) and smaller blood vessels 624B (e.g., capillaries).

Light detectors 606 may include optical fibers 612A-F, image sensor 614A-F (e.g., CMOS, CCD, etc.), and optical converters 616A-F (e.g., optical switch, lens, etc.).

Each of light sources 604 may include an optical fiber 618, and a light generator 620. Optical fiber 618 may be a multi-mode optical fiber having a core diameter of 50 µm, 62.5 µm, or some other diameter that is greater than 10 µm. In some implementations, optical fiber 618 is a multi-modal optical fiber having a core diameter of 1 mm or greater. Light generator 620 may be a continuous wave laser that is selectively chopped or operated to provide predetermined durations of illumination within tissue sample 602. Each of light sources 604 may be controlled by and communicate with processing logic 608 over communications channels X1A-B (collectively communications channels X1). Imaging system 600 may be implemented with a single light source 604A and may be implemented with one or more additional light sources, such as light source 604B. Optional light source 604B may use the same light generator 620A as light source 604A, or may have a different light generator 620B. Light generator 620B may be a different wavelength of light than the wavelength of light generator 620A, in an embodiment.

Figure 7:
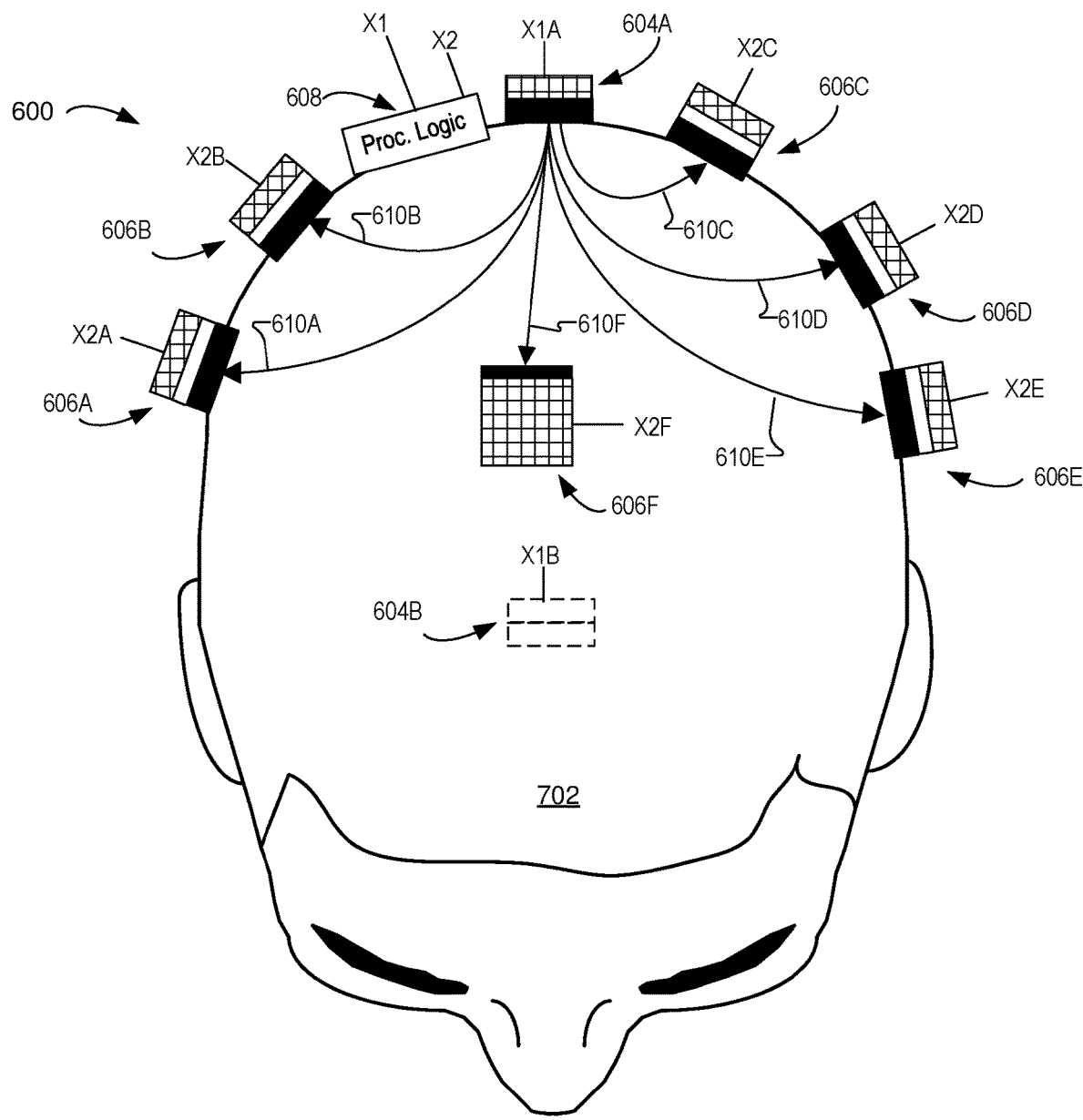
FIG. 7 illustrates an imaging system applied to a human head and configured to determine blood characteristics, in accordance with aspects of the disclosure.

FIG. 7 illustrates an example placement of components of imaging system 600 (shown in FIG. 6) in relationship to a human head, in accordance with an embodiment of the disclosure. FIG. 7 is a top-down view of a human head 702. Light source 604A may be positioned to provide light that is diffused within human head 702. Portions of the diffused light, such as measurement beams 610A-F may be captured by light detectors 606A-F at a variety of locations around human head 702. A wearable hat or other sensor carrying device may include system 600 so that system 600 can be worn as a wearable, in some embodiments. Other wearables may also include all or part of system 600.

Figure 8:
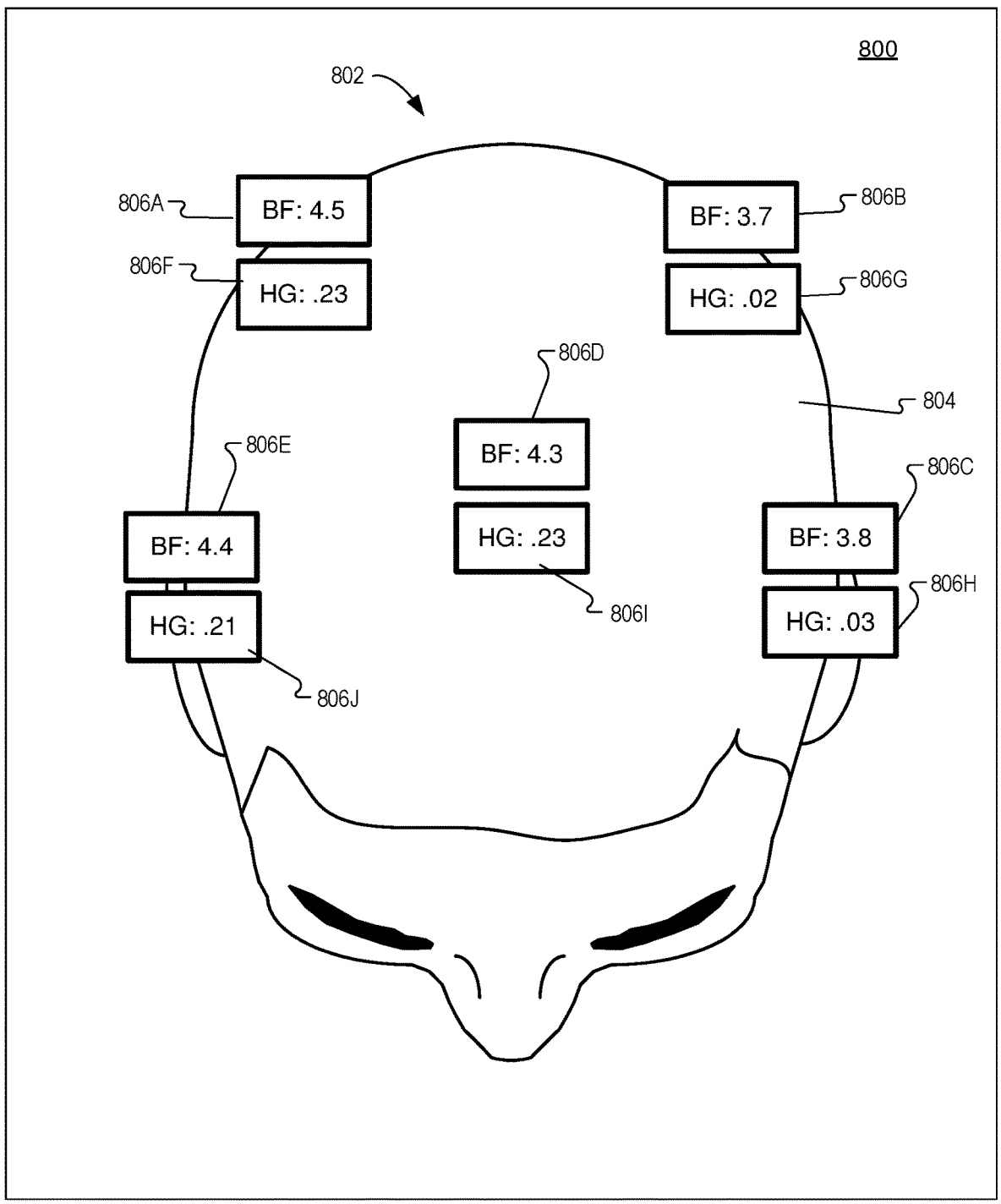
FIG. 8 illustrates a display of a composite image of blood characteristics values, in accordance with aspects of the disclosure.

FIG. 8 illustrates an example display 800 that includes a composite image 802 of a human head 804, to provide easily viewable/readable blood characteristics, in accordance with an embodiment of the disclosure. Composite image 802 may include a number of display values 806 (individually 806A, 806B, 806C, 806D, 806E, 806F, 806G, 806H, 806I, 806J). Display values 806A-E may be configured to display blood flow (BF) indices, rates, or volume. Display values 806F-J may be configured to display hemoglobin (HG) oxygenation values or rates. Display values 806 may be additionally or alternatively configured to display intensity and/or optical attenuation coefficients to indicate absolute or relative blood flow through a portion of human head 804, for example.

Figure 9:
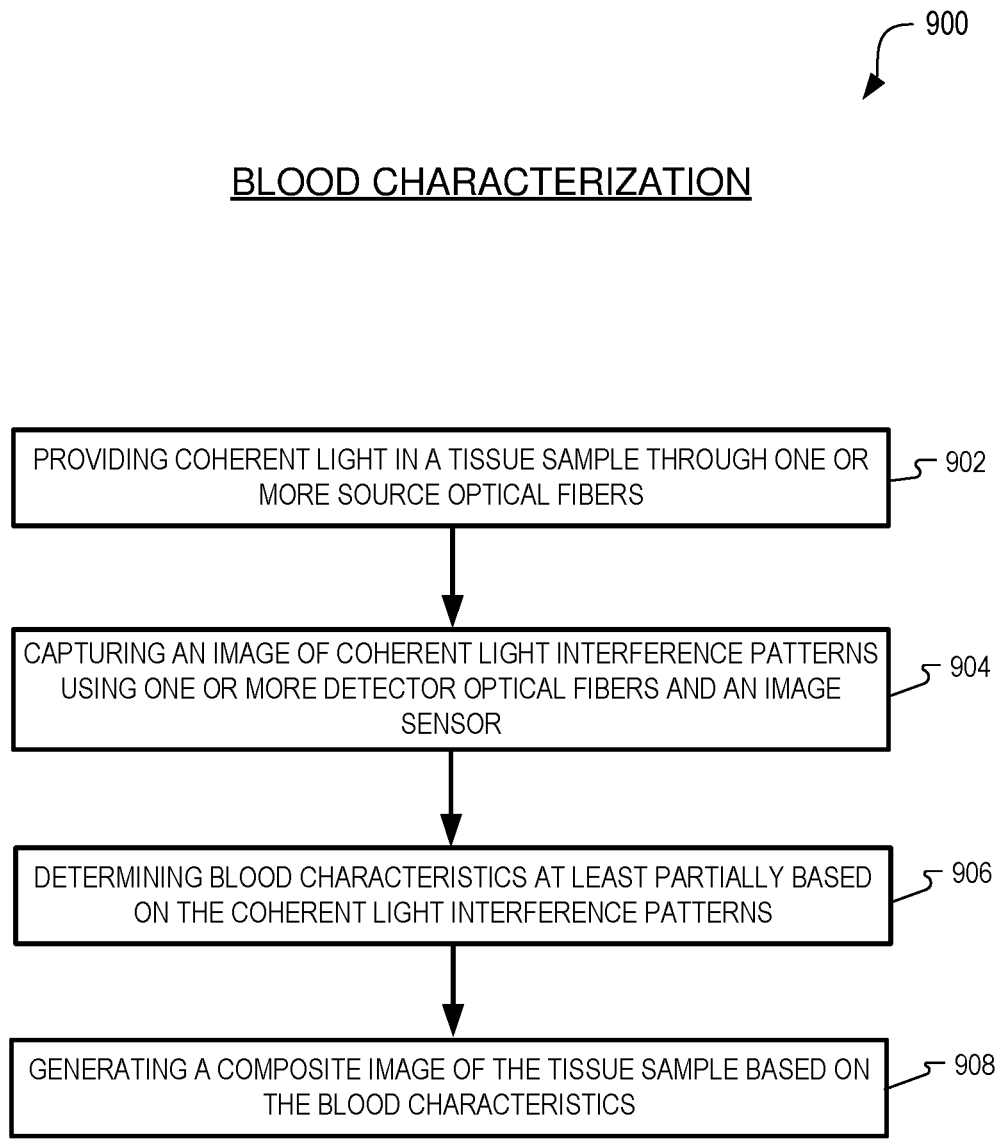
FIG. 9 illustrates a flow diagram of a process for determining blood characteristics from coherent light interference patterns, in accordance with aspects of the disclosure.

FIG. 9 illustrates a process 900 for determining blood characteristics from coherent light interference patterns, in accordance with an embodiment of the disclosure. The operations of process 900 may be performed in the order described or in another order, according to various embodiments.

At operation 902, process 900 includes providing coherent light in a tissue sample through one or more source optical fibers, according to an embodiment. An example of coherent light includes laser light where the emitted radiation includes waves vibrating in the same phase, same amplitude, and same wavelength. The laser light is emitted with wavelengths of 600-900 nm, in an embodiment. The laser light is configured to be emitted at 850 nm, in an embodiment. The laser light is provided with a pulse duration including the range of 10 µs to 100 µs, in an embodiment. The laser light is provided at one or more of multiple different pulses widths, including 10 µs, 20 µs, 40 µs, and 80 µs, in an embodiment.

At operation 904, process 900 includes capturing an image of coherent light interference patterns using one or more detector optical fibers and an image sensor, according to an embodiment. The one or more detector optical fibers are multi-mode optical fibers, for example, having a core diameter that is greater than 10 µm. Examples of multi-mode optical fiber include (e.g., glass or plastic) optical fibers having a core diameter of 50 µm, 62.5 µm, 200 µm, 1 mm, or the like. In one embodiment, the one or more detector optical fibers are single-mode optical fibers, for example, having a core diameter of 9 µm or less. The image sensor may be a CMOS or CCD image sensor.

At operation 906, process 900 includes determining blood characteristics at least partially based on the coherent light interference patterns, according to an embodiment. Coherent light interference patterns are analyzed by determining the speckle contrast of the image, for example, by dividing the standard deviation of the pixels of the image by the mean of the pixels of the image, in an embodiment.

At operation 908, process 900 includes generating a composite image of the tissue sample based on the blood characteristics, according to an embodiment. The composite image may include information from multiple images combined into a single image. In one implementation, the composite image is 3D image of voxels. In another implementation, the composite image is a 2D or 3D image that illustrates numerical values for one or more of speckle contrast, blood flow indices, hemoglobin oxygenation, and/or similar blood characteristics. Applying these techniques to specific parts of the body may facilitate diagnosis of health issues associated with decreased blood flow in one or more areas of the body.

Figure 10:
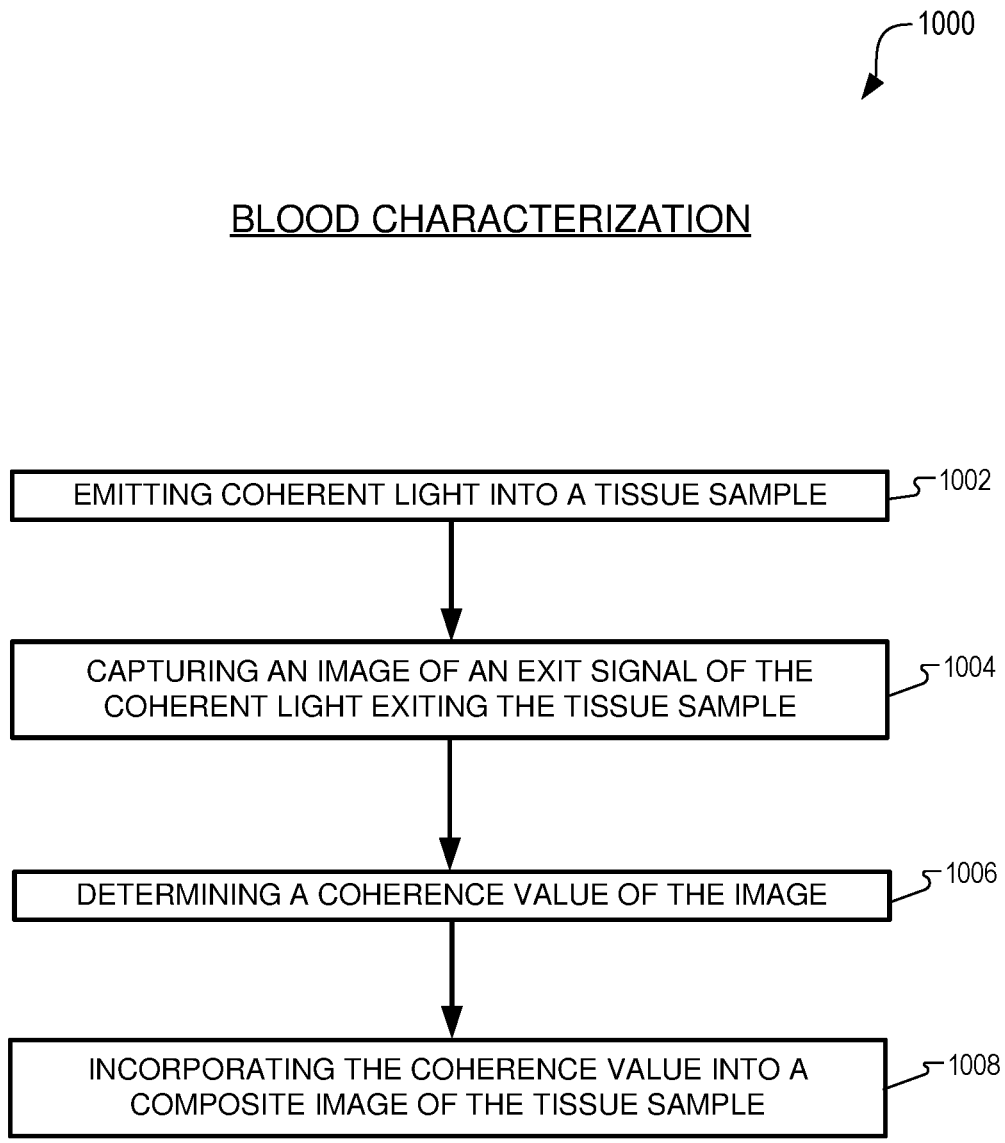
FIG. 10 illustrates a flow diagram of a process for determining blood characteristics from coherent light interference patterns, in accordance with aspects of the disclosure.

FIG. 10 illustrates a process 1000 for determining blood characteristics from coherent light interference patterns, in accordance with an embodiment of the disclosure. The operations of process 1000 may be performed in the order described or in another order, according to various embodiments.

At operation 1002, process 1000 includes emitting coherent light into a tissue sample, according to an embodiment. An example of coherent light includes laser light where the emitted radiation includes waves vibrating in the same phase, same amplitude, and same wavelength. The laser light is emitted with wavelengths of 600-900 nm, in an embodiment. The laser light is configured to be emitted at 850 nm, in an embodiment. The laser light is provided with a duration including the range of 1 µs to 30 µs, in an embodiment. The laser light is provided at one or more of multiple different pulses widths, including 10 µs, 20 µs, 40 µs, and 80 µs, in an embodiment.

At operation 1004, process 1000 includes capturing an image of an exit signal of the coherent light exiting the tissue sample, according to an embodiment. The exit signal may be captured using one or more detector optical fibers that are multi-mode optical fibers having, for example, a core diameter that is greater than 10 µm. Examples of multi-mode optical fiber include (e.g., glass or plastic) optical fibers having a core diameter of 50 µm, 62.5 µm, 200 µm, 1 mm, or the like. In one embodiment, the one or more detector optical fibers are single-mode optical fibers, for example, having a core diameter of 9 μm or less.

At operation 1006, process 1000 includes determining a coherence value of the image, according to an embodiment. A coherence value may correspond with coherent light interference patterns, which may be analyzed by determining the speckle contrast of the image, for example, by dividing the standard deviation of the pixels of the image by the mean of the pixels of the image, in an embodiment.

At operation 1008, process 1000 includes incorporating the coherence value into a composite image of the tissue sample, according to an embodiment. The composite image may include information from multiple images combined into a single image. In one implementation, the composite image is 3D image of voxels. In another implementation, the composite image is a 2D or 3D image that illustrates numerical values for one or more of speckle contrast, blood flow indices, hemoglobin oxygenation, and/or similar blood characteristics. Applying these techniques to specific parts of the body may facilitate diagnosis of health issues associated with decreased blood flow in one or more areas of the body.

The term "processing logic" (e.g. processing logic 108 or 608) in this disclosure may include one or more processors, microprocessors, multi-core processors, Application-specific integrated circuits (ASIC), and/or Field Programmable Gate Arrays (FPGAs) to execute operations disclosed herein. In some embodiments, memories (not illustrated) are integrated into the processing logic to store instructions to execute operations and/or store data. Processing logic may also include analog or digital circuitry to perform the operations in accordance with embodiments of the disclosure.

A "memory" or "memories" described in this disclosure may include one or more volatile or non-volatile memory architectures. The "memory" or "memories" may be removable and non-removable media implemented in any method or technology for storage of information such as computer-readable instructions, data structures, program modules, or other data. Example memory technologies may include RAM, ROM, EEPROM, flash memory, CD-ROM, digital versatile disks (DVD), high-definition multimedia/data storage disks, or other optical storage, magnetic cassettes, magnetic tape, magnetic disk storage or other magnetic storage devices, or any other non-transmission medium that can be used to store information for access by a computing device.

Communication channels may include or be routed through one or more wired or wireless communication utilizing IEEE 802.11 protocols, BlueTooth, SPI (Serial Peripheral Interface), I²C (Inter-Integrated Circuit), USB (Universal Serial Port), CAN (Controller Area Network), cellular data protocols (e.g. 3G, 4G, LTE, 5G), optical communication networks, Internet Service Providers (ISPs), a peer-to-peer network, a Local Area Network (LAN), a Wide Area Network (WAN), a public network (e.g. "the Internet"), a private network, a satellite network, or otherwise.

A computing device may include a desktop computer, a laptop computer, a tablet, a phablet, a smartphone, a feature phone, a smartwatch, a server computer, or otherwise. A server computer may be located remotely in a data center or be stored locally.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible non-transitory machine-readable storage medium includes any mechanism that provides (i.e., stores) information in a form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An imaging system comprising:
   a pulsed laser configured to emit pulsed laser light;
   a source optical fiber coupled to the pulsed laser and configured to deliver the pulsed laser light into a tissue sample;
   a detector optical fiber configured to receive diffuse laser light from portions of the pulsed laser light that exits the tissue sample;
   an image sensor coupled to the detector optical fiber and configured to capture an image of the diffuse laser light exiting the tissue sample; and
   processing logic configured to:
   receive the image from the image sensor;
   determine a coherence value of the diffuse laser light in the image; and
   determine blood flow rates for the tissue sample at least partially based on the coherence value, wherein the pulsed laser light includes one or more pulses of coherent light having a duration of 10 μs to 100 μs, wherein the one or more pulses support a correlation of the coherence value to the determined blood flow rates.

2. The imaging system of claim 1, wherein the detector optical fiber is a multi-mode fiber.

3. The imaging system of claim 1, wherein the pulsed laser light is a near-infrared laser light, and wherein the image sensor includes a filter to block light outside of a linewidth of the pulsed laser light.

4. The imaging system of claim 1 further comprising:
   a second image sensor configured to capture a second image of a second diffuse laser light exiting the tissue sample, wherein the image sensor is disposed at a first exit location of the tissue sample and the second image sensor is disposed at a second exit location of the tissue sample, wherein the processing logic is configured to receive the second image from the second image sensor, wherein the image and the second image are captured concurrently.

5. The imaging system of claim 1, wherein the coherence value of the diffuse laser light in the image is determined as a speckle contrast value, which is determined as a standard deviation of pixel values of the image divided by a mean of the pixel values of the image.

6. The imaging system of claim 1, wherein the image sensor is configured to capture reference beam laser light and the diffuse laser light as an interference pattern of the reference beam laser light with the diffuse laser light,
    wherein the processing logic is further configured to determine the coherence value of the diffuse laser light in the image by determining a contrast value between the interference pattern in the image.

7. The imaging system of claim 1, wherein the processing logic is further configured to generate a composite image from multiple captures of the coherence value, wherein the composite image represents the blood flow rates in the tissue sample, wherein the coherence value increases as the blood flow rates decrease.

8. An imaging method comprising:
    emitting pulsed coherent laser light into a tissue sample, wherein the pulsed coherent laser light is emitted by a pulsed laser;
    capturing, with an image sensor, an image of an exit signal of the pulsed coherent laser light exiting the tissue sample;
    determining blood flow rates for the tissue sample at least partially based on a coherence value of the image captured by the image sensor; and
    incorporating the coherence value into a composite image of the tissue sample, wherein emitting the pulsed coherent laser light includes providing one or more pulses of the pulsed coherent laser light having a duration of 10 µs to 100 µs, wherein the one or more pulses support a correlation of the coherence value to the determined blood flow rate of the tissue sample.

9. The imaging method of claim 8, wherein the pulsed coherent laser light is laser light having a wavelength in a range of 600-900 nm.

10. The imaging method of claim 8, wherein at least a portion of the exit signal previously propagated deeper than two centimeters deep into the tissue sample.

11. The imaging method of claim 8, wherein determining the coherence value includes determining a speckle contrast value for the image, wherein the speckle contrast value is a standard deviation of pixel values in the image divided by an average intensity of the pixel values in the image.

12. The imaging method of claim 8, wherein the composite image includes a two-dimensional or three-dimensional image of a body part with one or more coherence values represented on the image of the body part.

13. The imaging method of claim 8 further comprising:
    emitting a reference beam of coherent light,
    wherein capturing the image includes capturing the reference beam with the exit signal in the image,
    wherein determining the coherence value for the image includes determining a contrast value between fringe patterns in the image.

14. The imaging method of claim 8, wherein the exit signal propagates from the tissue sample to the image sensor in a detector optical fiber having a diameter of greater than 10 microns.

15. An imaging system comprising:
    a pulsed laser configured to emit pulsed laser light;
    one or more source optical fibers coupled to the pulsed laser and configured to deliver the pulsed laser light into tissue;
    a detector optical fiber configured to receive diffuse laser light from portions of the pulsed laser light that exits the tissue;
    an image sensor coupled to the detector optical fiber and configured to capture an image of the diffuse laser light exiting the tissue; and
    processing logic configured to:
        receive the image from the image sensor;
        determine a coherence value of the diffuse laser light in the image; and
        determine blood flow rates for the tissue at least partially based on the coherence value, wherein the pulsed laser light includes one or more pulses of coherent light having a duration of 10 µs to 1000 µs.

16. The imaging system of claim 15, wherein the processing logic is further configured to generate a composite image of the tissue based on the blood flow rates of the tissue; wherein the processing logic is further configured to generate a composite image of the tissue based on the determined blood flow rates of the tissue.

* * * * *